(12) United States Patent
Jedweb et al.

(10) Patent No.: US 8,597,259 B2
(45) Date of Patent: Dec. 3, 2013

(54) FLOW CONTROLLER

(75) Inventors: Michael Jedweb, Lausanne (CH); Giancarlo Gagliardoni, Caracas (VE); Giuseppe Antonio Nichetti, Lausanne (IT)

(73) Assignee: Nestec S.A., Vevey (CH)

( * ) Notice: Subject to any disclaimer, the term of this patent is extended or adjusted under 35 U.S.C. 154(b) by 399 days.

(21) Appl. No.: 12/446,686

(22) PCT Filed: Nov. 5, 2007

(86) PCT No.: PCT/EP2007/061889
§ 371 (c)(1),
(2), (4) Date: Apr. 22, 2009

(87) PCT Pub. No.: WO2008/055876
PCT Pub. Date: May 15, 2008

(65) Prior Publication Data
US 2011/0098661 A1      Apr. 28, 2011

(30) Foreign Application Priority Data
Nov. 7, 2006   (EP) .................................... 06123583

(51) Int. Cl.
*A61M 5/00*      (2006.01)
(52) U.S. Cl.
USPC ............................................. 604/250; 251/8
(58) Field of Classification Search
USPC ................ 604/250; 251/4, 8, 9; 606/157, 158
See application file for complete search history.

(56) References Cited

U.S. PATENT DOCUMENTS

| 3,215,395 | A | | 11/1965 | Gorbar |
| 3,584,830 | A | | 6/1971 | Koehn |
| 4,091,815 | A | | 5/1978 | Larsen |
| 4,312,493 | A | * | 1/1982 | Stauffer ........................... 251/8 |
| 4,390,019 | A | | 6/1983 | Leveen |
| 4,490,143 | A | * | 12/1984 | Quinn et al. .................. 604/270 |
| 6,767,354 | B2 | * | 7/2004 | Johanson et al. ............ 606/179 |
| 7,954,210 | B2 | * | 6/2011 | Ruffing .......................... 24/489 |

FOREIGN PATENT DOCUMENTS

| DE | 103 49 761 A1 | 6/2005 |
| FR | 2 613 939 A | 10/1988 |
| JP | 55-135287 | 4/1982 |
| JP | 2003-069012 | 10/2004 |
| WO | WO 2006081866 A1 * | 8/2006 ............ A61M 39/28 |

OTHER PUBLICATIONS

International Report on Patentability received in corresponding PCT Application No. PCT/EP07/61889 filed Nov. 5, 2007.
International Search Report received in corresponding PCT Application No. PCT/EP07/61889 filed Nov. 5, 2007.

* cited by examiner

*Primary Examiner* — Emily Schmidt
(74) *Attorney, Agent, or Firm* — K&L Gates LLP

(57) ABSTRACT

A device for controlling the rate of flow of a liquid in a flexible tube comprising two opposed surfaces between which the tube is received in use wherein the surfaces are elongated in the direction of flow of the liquid in the tube and are either parallel to one another or arranged so that in use the included angle does not exceed 40°, and means for varying the distance between the surfaces so as to compress the tube between them by the desired amount.

8 Claims, 2 Drawing Sheets

FLOW CONTROLLER

This invention relates to a device for controlling the rate of flow of a liquid in a flexible tube. More specifically, this invention relates to a device for controlling the rate of flow of a liquid enteral nutritional composition through the tube which is used to administer the composition to the patient.

Due to a variety of diseases, insults, and complications, patients may not be able to obtain the necessary nutrition by ingesting food through the mouth, e.g., eating food. Therefore, it is known to provide clinical nutrition both enterally and parenterally. A conventional means of providing such nutrition enterally is by use of a feeding tube connected at one end to a supply or source of liquid nutrition and at the other end to a nasogastric feeding tube or percutaneous endoscopic gastrostomy tube of the patient.

It will be understood it is necessary to control the rate of flow of the enteral composition through the tube and thus to the patient. In the extreme case of free flow, the patient can quite literally drown in the fluid and in the extreme case of too low a flow rate, the patient can become severely undernourished. Between these two extremes, it is usually desired to administer the composition at a particular flow rate having regard to the properties of the composition being administered and the needs of the patient. Typical flow rates are between 100 and 300 ml/hr although flow rates as low as 50 ml/hr may occasionally be required.

The nutritional composition may be administered with the help of a pump or under the action of gravity. When a pump is used, the flow rate can be accurately set and nursing staff can be confident that once the desired flow rate has been established it will be maintained until all the feed has been delivered to the patient. However, the use of a pump adds considerably to expense and therefore pumps are only used when absolutely necessary, for example with very viscous compositions which will not otherwise reach acceptable flow rates or when accuracy is clinically necessary.

However, even for feeds which can be administered under the action of gravity, it is generally necessary to control the flow rate. To achieve this in the absence of a pump a roller clamp is usually provided with the feeding tube. Many different designs of roller clamp are known for example from U.S. Pat. Nos. 3,984,081, 4,919,389 and German Patent Application No. 19621910A1. Essentially, these devices comprise an elongate housing which receives the feeding tube and a member of circular cross-section mounted in the housing such that it can be moved up and down the length of the housing whereby the curved surface of the member with circular cross section compresses the tube to the desired extent. This reduces the cross-sectional area of the tube available for flow and thus reduces the flow rate.

Feed tubes are generally made of soft plastics materials such as PVC. In the uncompressed state, the tubes have a generally circular cross-section with an internal diameter typically of the order of 3 to 4.5 mm. When compressed by a roller clamp, the lumen of the tube is pinched and assumes a generally kidney-shaped cross-section. The cross-sectional area of the tube available for flow is reduced as desired but, over time, the plastics material of which the tube is made starts to yield and cold flow at the areas under high stress. In other words, the material of the tube "creeps" around the point at which it is pinched by the roller clamp and the tube assumes a generally U-shaped cross-section at the pinch point. Over time this reduces the cross-sectional area available for flow and thus reduces flow rate even though the setting of the roller clamp has not changed. Further some dimensions of the lumen approach the value of about 0.5 mm which is the same order of magnitude as components such as dietary fibres which are often found in nutritional compositions. It will be appreciated that this entails a risk of nucleation of such particles and ultimately complete blocking of the tube at the pinch point.

In practice, with feeds containing fibres and other large particles such blocking may occur about once an hour. Each time the tube blocks, the nurse has to open the roller clamp to clear the block then reset the roller clamp which results in a considerable amount of lost time as well as inconvenience to both patient and nurse.

Therefore, there is a need to provide an alternative construction for a flow controller which does not suffer from these disadvantages.

SUMMARY OF THE INVENTION

The present inventors have surprisingly discovered that if the feed tube is compressed by opposed generally parallel surfaces each of which is elongated in the direction of flow, the tube can be compressed in such a way that the problems of cold flow are minimized, a flow rate which is stable over many hours can be achieved and flow rates as low as 50 ml/hr can be achieved with minimal risk of blockages.

Accordingly, the present invention provides a device for controlling the rate of flow of a liquid in a flexible tube comprising two opposed surfaces between which the tube is received in use wherein the surfaces are elongated in the direction of flow of the liquid in the tube and are either parallel to one another or arranged so that in use the included angle does not exceed 40°, and means for varying the distance between the surfaces so as to compress the tube between them by the desired amount.

The invention further extends to a set for enteral feeding comprising a flexible tube and a device for controlling the rate of flow of a liquid in the tube wherein the device comprises two opposed surfaces between which the tube is received which surfaces are elongated in the direction of flow of the liquid in the tube and are either parallel to one another or arranged so that in use the included angle does not exceed 40°, and means for varying the distance between the surfaces so as to compress the tube between them by the desired amount.

Without wishing to be bound by theory, the inventors believe that, using a device according to the invention, the geometry presented to the liquid as it approaches and passes through the part of the tube compressed by the device is such that the liquid encounters a smoothly reduced cross-section thus allowing friction to decelerate the liquid. In other words, contrary to what happens with the conventional roller clamp described above, the liquid does not encounter any sharp corners which could act as nucleation sites for particles or fibres as it approaches and passes through the part of the tube compressed by the device.

Preferably the length of the surfaces in contact with the tube in use is at least five times greater than the internal diameter of the tube.

Preferably the tube includes a portion made from a highly elastic material with a low visco-elastic response such as silicone or a synthetic silicone replacement material and that portion of the feed tube is received within the flow controller in use.

If the opposed surfaces are not parallel, the included angle preferably does not exceed 35°, more preferably 26°, when the device is in use.

The opposed surfaces are preferably generally flat.

FIGURES

DETAILED DESCRIPTION OF THE INVENTION

Figure 1:
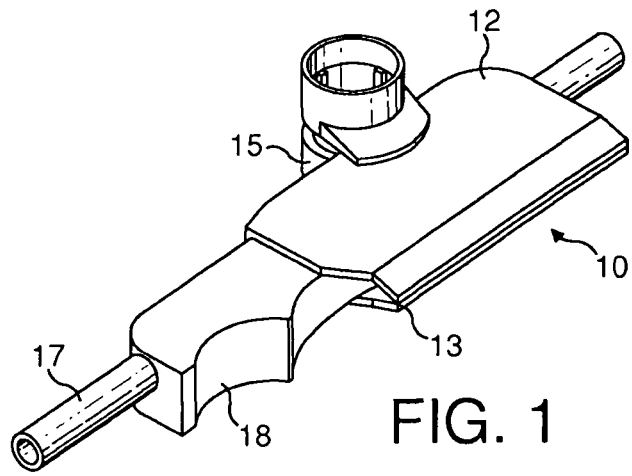
FIGS. 1 and 2 show in perspective view and cross-sectional view respectively a first embodiment of flow controller according to the invention.

In the present specification, the following words are given a definition that must be taken into account when reading and interpreting the description, examples and claims.

"Elongated in the direction of flow of the liquid in the tube": the dimension of the surface which extends in the direction of flow of the liquid in the tube is larger than the dimension which extends transverse to the direction of flow of the liquid.

"Generally flat" means that those portions of the opposed surfaces which contact the tube in use are flat but does not exclude the presence of minor imperfections or the presence of, for example, a channel with a radius of curvature of the same order of magnitude as the radius of the tube for use as a guide for the tube.

"Included angle" means the angle between the opposed surfaces when the device is in use in the event that the opposed surfaces are not parallel.

As noted above, preferably the length of the opposed surfaces in contact with the tube in use is at least five times greater than the internal diameter of the tube. Tubes used for enteral feeding typically have an internal diameter of between 3 and 4.5 mm, therefore the length of the opposed flat surfaces in contact with the tube when the device is in use is preferably at least 15 mm, more preferably at least 25 mm and most preferably between 40 and 45 mm.

To further reduce the risk of blocking of the tube in use, it preferably includes at least a portion made from an elastic material such as silicone or a synthetic silicone replacement material such as DEHP-free DINCH supplied by Action Technology. In use, this portion is received within the flow controller.

In an embodiment, the opposed surfaces are hinged along one long edge and the means for varying the distance between them comprises a screw-threaded bolt attached to the opposite long edge of one surface and adapted to pass through an aperture in the opposite long edge of the other surface and a nut which may be screwed onto the bolt to reduce the distance between the surfaces.

Alternatively, each of the opposed surfaces may be provided with an aperture in the long edge opposite the hinge and the means for varying the distance between them may comprise a double-ended screw-threaded bolt provided with a fixed nut between the screw threads such that the screw threaded ends of the bolt may be received in the apertures and the bolt may be rotated using the fixed nut to vary the distance between the surfaces.

In another embodiment, the device comprises a cylindrical housing with a cavity running along its length of rectangular cross-section which cross-section increases in a linear fashion from one end to the other and an insert of rectangular cross-section which likewise and triangular longitudinal section increases in a linear fashion from one end to the other. The insert is adapted to be received in the cavity whereby the said opposed surfaces are constituted by a surface of the cavity and a parallel surface of the insert. The means for varying the distance between the opposed surfaces comprises a collar upon which the insert is mounted such that it can be inserted in the cavity and moved along the length of the cavity by movement of the collar.

Preferably in this case the end of the housing from which the insert is introduced into the cavity is provided with a screw thread, the collar is provided with a reciprocal screw thread and the insert is mounted on the collar such that it can rotate relative thereto whereby the insert may be moved along the length of the cavity by engagement of the screw threads and rotation of the collar relative to the housing.

The invention will now be illustrated by reference to the drawings.

Figure 2:
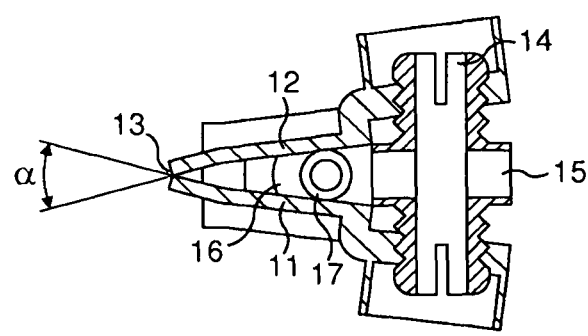

FIGS. 1 and 2 show in perspective view and cross-sectional view respectively an embodiment of a flow controller 10 according to the invention. The flow controller comprises two opposed generally flat surfaces 11 and 12 arranged with a variable included angle α between them. The surfaces 11 and 12 are joined along one edge by a hinge 13 and connected at their opposite edges by a double-ended grub screw 14 provided with adjustment means 15. The screw 14 is received in threaded apertures in each of surfaces 11 and 12 such that the adjustment means 15 may be rotated to vary the included angle between the surfaces by moving surfaces 11 and 12 towards or away from one another. The surfaces 11 and 12 are provided with guides 16 which receive the feed tube 17. The flow controller also includes at one end an ergonomically designed hollow grip portion 18 to assist the nurse or other care giver to handle the flow controller efficiently.

In use, the flow controller is supplied pre-assembled round the tube. The nurse or other care-giver will connect the tube to the feed to be administered and check the flow rate by counting the number of drops passing though the drip chamber of the tube in a given time and will adjust the flow rate to the desired value by rotating the adjustment means 15 to increase or decrease the degree of compression of the tube accordingly. In the position shown in FIG. 2, the adjustment means has been rotated such that surfaces 11 and 12 grip the tube 17 without compressing it and the angle α is 26° for a tube with an internal diameter of 3 mm.

It will be appreciated that the flow controller can be closed to a point at which there is no flow at all through the tube which may be convenient for example when the care-giver is changing the supply of the feed to be administered. In this case the angle α would be 9° for a tube with an internal diameter of 3 mm.

In a variation of this embodiment (not shown), the means for varying the included angle between the opposed flat surfaces may comprise a single-ended grub screw mounted on the free long edge of one surface and adapted to pass through an aperture in the long edge of the opposite surface and a nut which may be screwed up and down the free end of the grub screw to vary the distance between the surfaces.

Figure 3:
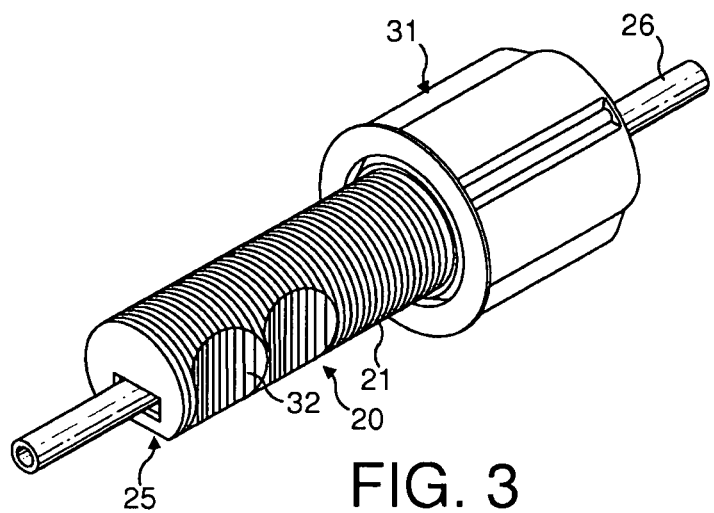
FIGS. 3 and 4 show in perspective view and cross-sectional view respectively a second embodiment of flow controller according to the invention.
Figure 4:
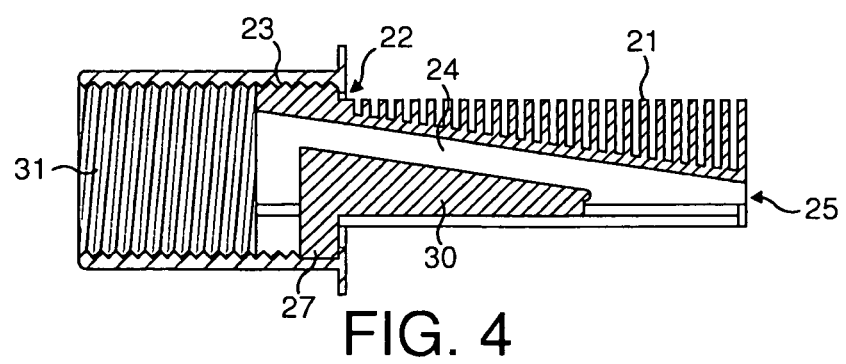

FIGS. 3 and 4 show in perspective and cross-sectional view respectively a second embodiment of a flow controller 20 according to the invention having a generally cylindrical housing 21 provided at one end 22 with a screw thread 23. A cavity 24 of varying rectangular cross-section runs along the length of the housing. The cross-section of this cavity increases at a constant angle along its length with the distance between the roof and the base being at its largest at the end 22 and at its smallest at the other end 25. A longitudinally extending guide channel (not shown) is provided in housing 21 and connects cavity 24 with the exterior.

An insert 30 with a rectangular cross-section which likewise varies in a linear fashion from one end to the other is slidably received in the cavity 24 of cylindrical housing 21. The insert comprises two opposed surfaces arranged such that the included angle between them is the same as the included angle between the roof and base of the cavity 24. The insert is provided at its end of greatest cross-section with a neck which protrudes through the guide channel and terminates in a lug 27. Stops (not shown) are provided at each end of the cavity 24 so that insert 30 is captured within cylindrical housing 21. It may be seen that the roof of cavity 24 and the upper surface of the insert form opposed parallel surfaces the distance between which can be increased or decreased by moving the insert in and out of the cavity.

As with the embodiment shown in FIGS. 1 and 2, in use the flow controller is supplied already assembled round the tube 26 (FIG. 3) with the insert 30 captured within cylindrical housing 21 and the lug 27 located in a threaded collar 31 such that rotation of the collar 31 round screw-thread 23 slides the insert 30 in and out of the cavity 24 to compress the feed tube by the desired amount between the upper surface of the insert and the roof of the cavity. As with the embodiment of FIGS. 1 and 2, the nurse or other care-giver will connect the tube to the feed to be administered, check the flow rate by counting the number of drops passing though the drip chamber and adjust the flow rate to the desired value, in this case by rotating the collar 31 to move the insert 30 in or out of the cavity 24 to respectively increase or decrease the degree of compression of the tube accordingly.

Further, as with the embodiment shown in FIGS. 1 and 2, the flow controller of FIGS. 3 and 4 also includes at one end ergonomic finger grips 32.

Further, as with the embodiment shown in FIGS. 1 and 2, the insert can be slid into the cavity such that the tube is compressed to the extent that the flow is completely interrupted.

The invention claimed is:

1. A device for controlling the rate of flow of a liquid in a flexible tube, the device comprising:
    two opposed surfaces between which the tube is received in use, wherein the opposed surfaces are generally flat, are elongated in the direction of flow of the liquid in the tube, and are either parallel to one another or arranged so that in use the included angle does not exceed 40°, wherein the opposed surfaces are hinged along one long edge and each provided with a threaded aperture in a long edge opposite the hinge; and
    means for varying a distance between the surfaces so as to compress the tube between them by a desired amount, wherein the means comprises a double-ended grub screw provided with adjustment means in the middle of the double-ended grub screw such that the ends of the grub screw may be received in the apertures and the adjustment means may be rotated to vary the distance between the surfaces.

2. The device of claim 1, wherein the included angle does not exceed 35°.

3. The device of claim 1, wherein the included angle does not exceed 26°.

4. The device of claim 1, wherein the length of the opposed surfaces in contact with the tube in use is at least five times greater than the internal diameter of the tube.

5. The device of claim 1, wherein the opposed surfaces are parallel to one another.

6. A set for enteral feeding, the set comprising:
    a flexible tube; and a device for controlling the rate of flow of a liquid in the flexible tube, the device comprising
    two opposed surfaces between which the tube is received in use, wherein the opposed surfaces are generally flat, are elongated in the direction of flow of the liquid in the tube, and are either parallel to one another or arranged so that in use the included angle does not exceed 40°, wherein the opposed surfaces are hinged along one long edge and each provided with a threaded aperture in a long edge opposite the hinge, and
    means for varying a distance between the surfaces so as to compress the tube between them by a desired amount, wherein the means comprises a double-ended grub screw provided with adjustment means in the middle of the double-ended grub screw such that the ends of the grub screw may be received in the apertures and the adjustment means may be rotated to vary the distance between the surfaces.

7. The set of claim 6, wherein the flexible tube includes a portion made from an elastic material such as silicone or a synthetic silicone replacement material.

8. The set of claim 6, which is supplied ready-assembled with the tube located within the device.

* * * * *